US00PP10411P

United States Patent [19]

Swartz et al.

[11] Patent Number: Plant 10,411

[45] Date of Patent: May 26, 1998

[54] RASPBERRY PLANT NAMED 'ANNE'

[76] Inventors: Harry Jan Swartz, 16022 Jerald Rd., Laurel, Md. 20707; Joseph A. Fiola, 1400 Paterson Ave., Whiting, N.J. 08759; Herbert D. Stiles, 811 Brunswick Ave., Blackstone, Va. 23824; Brian R. Smith, 311 N. Dallas St., River Falls, Wis. 54022

[21] Appl. No.: 630,179

[22] Filed: Apr. 10, 1996

[51] Int. Cl.[6] ..... A01H 5/00

[52] U.S. Cl. ..... Plt./46.2

[58] Field of Search ..... Plt./46.2

[56] References Cited

U.S. PATENT DOCUMENTS

P.P. 8,062 12/1992 Ackerman ..... Plt./46.2

*Primary Examiner*—James R. Feyrer

*Attorney, Agent, or Firm*—Marian P. Marks; Sana A. Pratt

[57] ABSTRACT

Ths invention relates to a new and distinct fall bearing golden fruited raspberry cultivar named 'Anne' which is capable of producing fruit on primocanes, the fruit being larger and more cohesive than that of the standard cultivars. The cultivar is characterized by moderate suckering ability, and its round-conic, light colored and symmetrical fruit. Additionally, it is characterized by its sparsely thorny upright canes, with fall fruit appearing on the upper quarter of the cane.

4 Drawing Sheets

ORIGIN OF THE NEW CULTIVAR

The new cultivar of fall bearing golden raspberry originated from a controlled cross at the University of Maryland Greenhouses in College Park, Md. The cross, "EF", was 'Amity'×'Glen Gerry' and was made in winter of 1989. This year was designated "J", as part of the Univeristy of Maryland at College Park; Rutgers University of New Brunswick, N.J.; Virginia Polytechnic Institute and State University, Southern Piedmont Agricultural Research and Education Center at Blackstone; and the University of Wisconsin at River Falls cooperative breeding program. The clone was the first of the progeny selected in 1991 at the Virginia Polytechnic Institute and State University near Blackstone, and was therefore designated '-b1'. Thus the complete breeding designation was "JEF-b1".

The new cultivar has been reproduced asexually by tissue culture techniques and tested in evaluation fields first by the cooperating breders, and then by licensed evaluators. Through the several thousand plants produced by tissue culture and standard asexually reproduced plants from root suckers, no off-type phenotype plants have been noted.

Upon agreement of all cooperators and representatives, the seedling clone "JEF-b1" will be designated cultivar 'Anne'.

SUMMARY OF THE NEW CULTIVAR

This application relates to a new and distinct golden fruited, fall bearing raspberry cultivar, botanically known as *Rubus ideaus* L. The following characteristics are outstanding:

1. Production of fruit on primocanes which is much more cohesive than the standard fall bearing cultivars currently in widespread use.

2. In warmer climates, fruit is larger and more flavorful than that of currently used fall bearing cultivars.

The following characteristics are distinguishing and can be useful for cultivar identification.

1. Plants are moderately suckering, producing half to 75% as many canes as 'Heritage'.

2. Fruit is round-conic, very cohesive, light colored and symmetrical. Druplets will often tear in half before separating from the neighboring druplets.

3. Fruit has an even collar.

4. Canes are light green colored and upright, with only a few thorns per node, and with fall fruit on the upper quarter of the cane.

5. Compared to other fall bearing cultivars, leaf serration is more complex with more acute angles at the points, similar to the non-fall bearing parent 'Glen Gerry'.

BRIEF DESCRIPTION OF THE PHOTOGRAPHS

The accompanying photographs show typical characteristics of the new variety:

Figure 5:
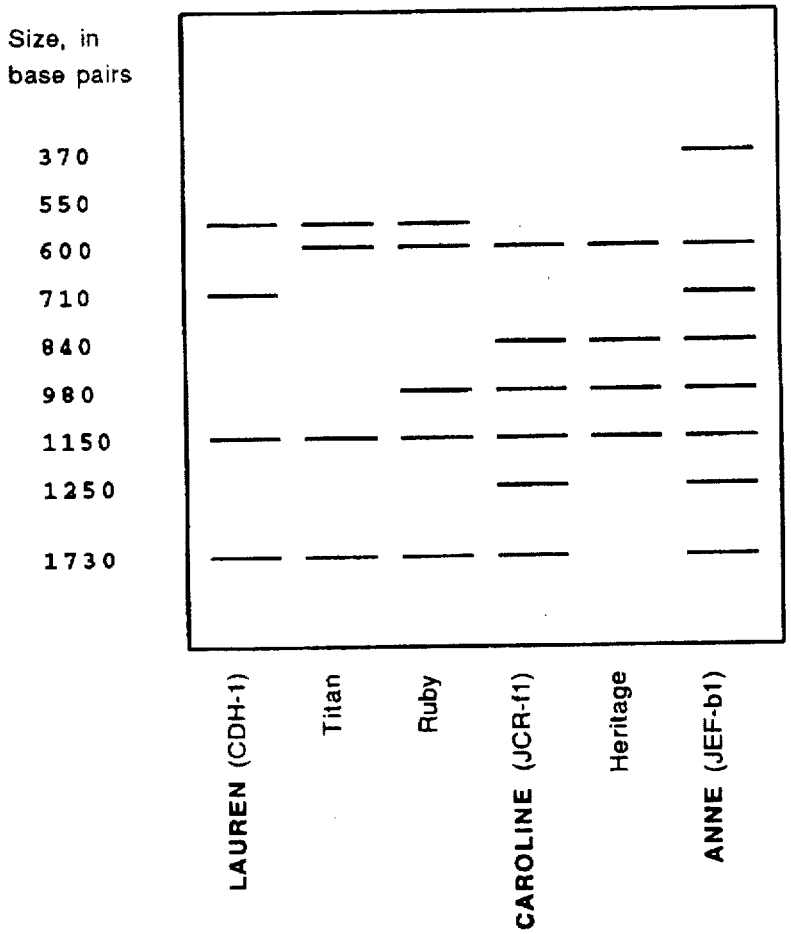

The FIG. 5 depicts the DNA fingerprints of JEF-b1, 'Heritage', 'Ruby', and several other concurrently released raspberry cultivars.

DESCRIPTION OF THE NEW CULTIVAR

The following is a detailed description of the new cultivar, including fruit production, together with the cultivar's morphological characteristics. The characteristics of the cultivar are compared to the standard used in the area: 'Hertiage'. This description is based on information provided by cooperating scientists from plants grown in fields at Queenstown, Md., Cream Ridge, N.J., Blackstone, Va. and River Falls, Wis., Rock Hall, Pa., and from plants grown in the greenhouse at College Park.

Figure 1:
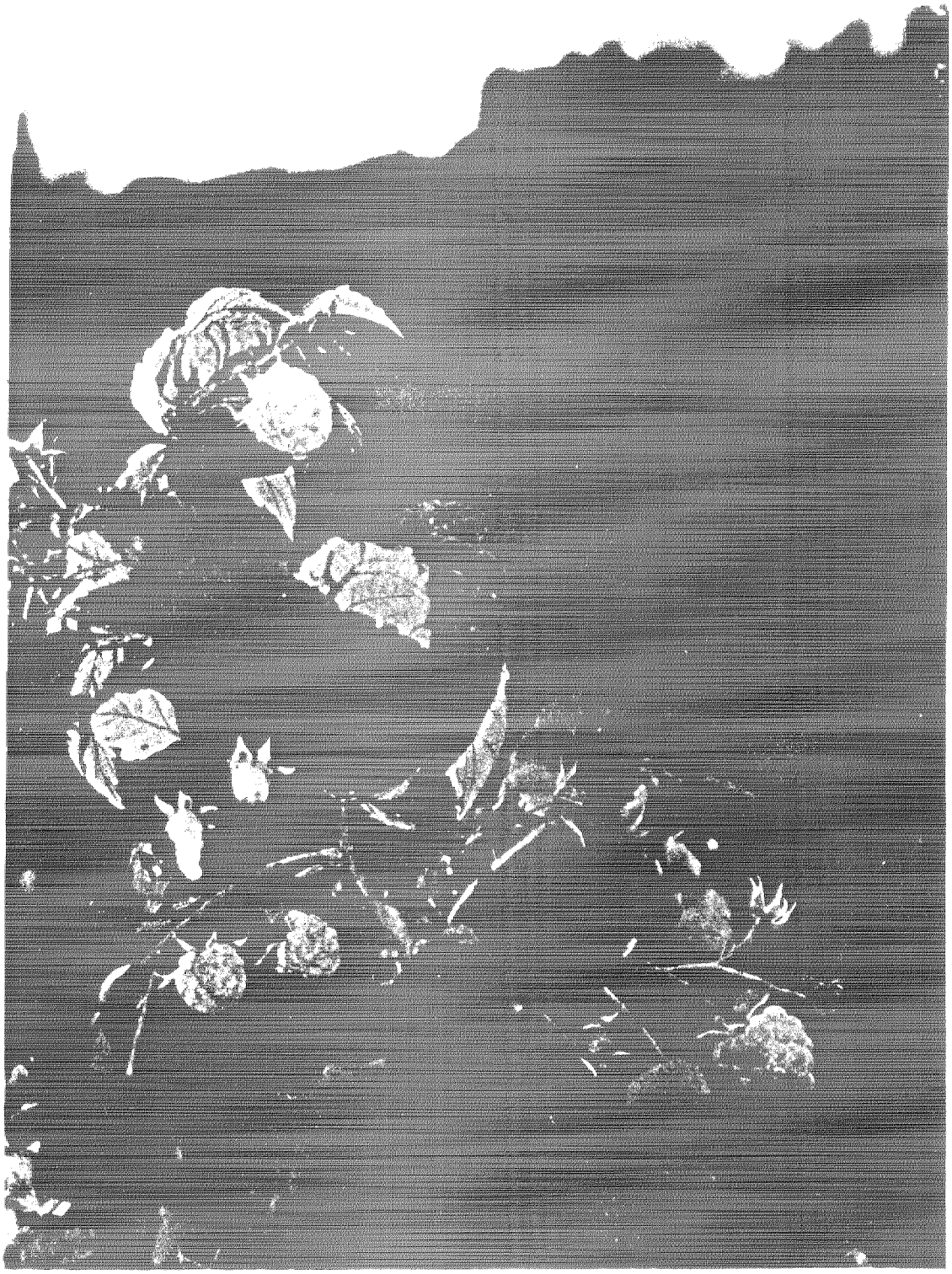
FIG. 1 shows a fruiting cluster of JEF-b1, showing the exposure of the fruit.
Figure 2:
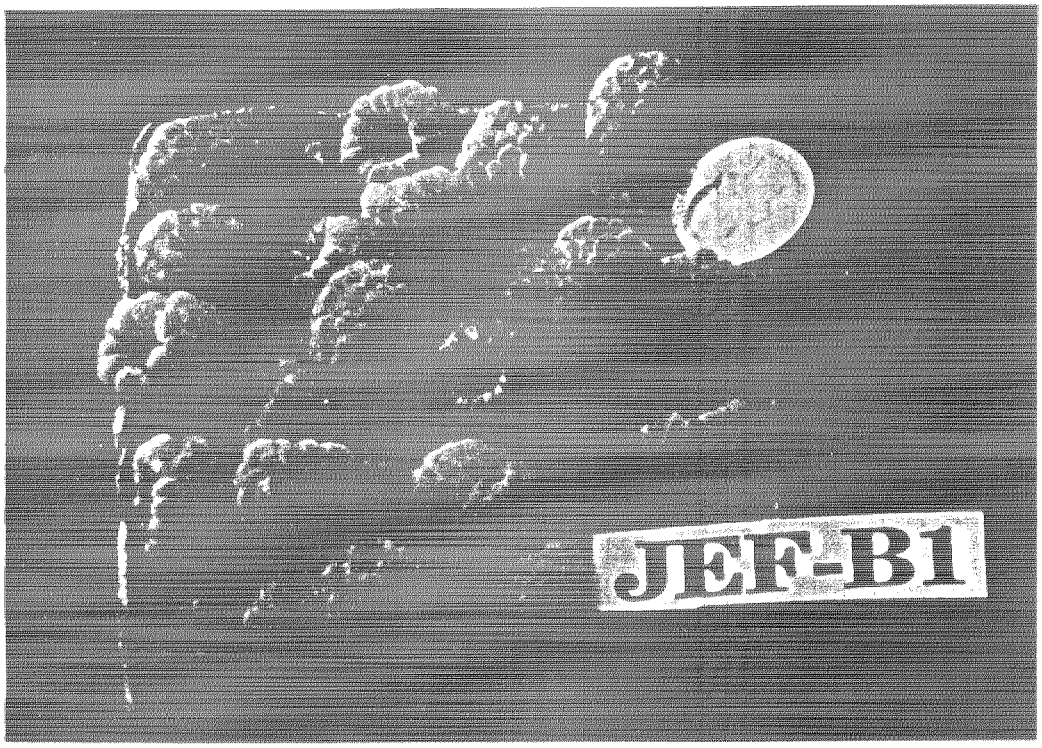
FIG. 2 shows the harvested fruit of JEF-b1.
Figure 3:
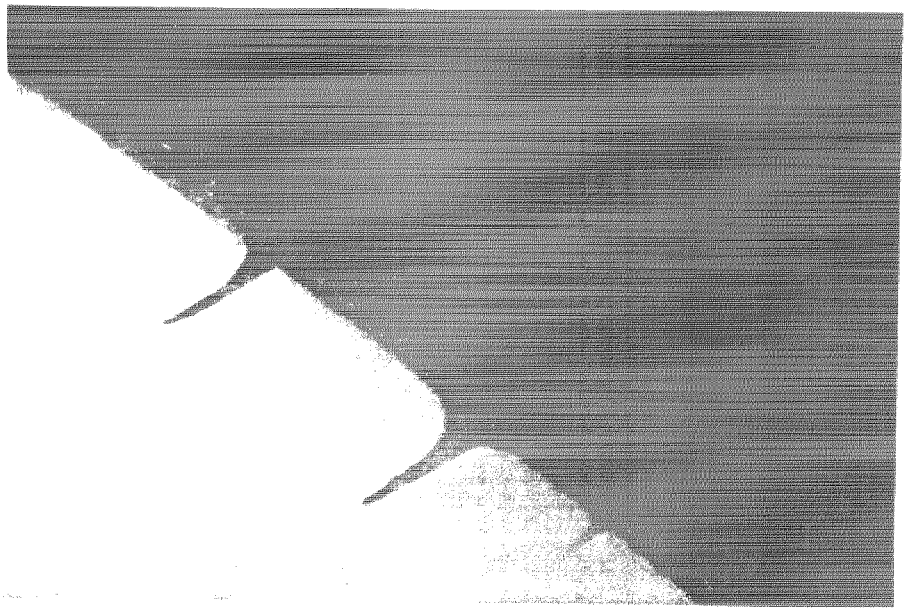
FIG. 3 shows the thorns of JEF-b1.
Figure 4:
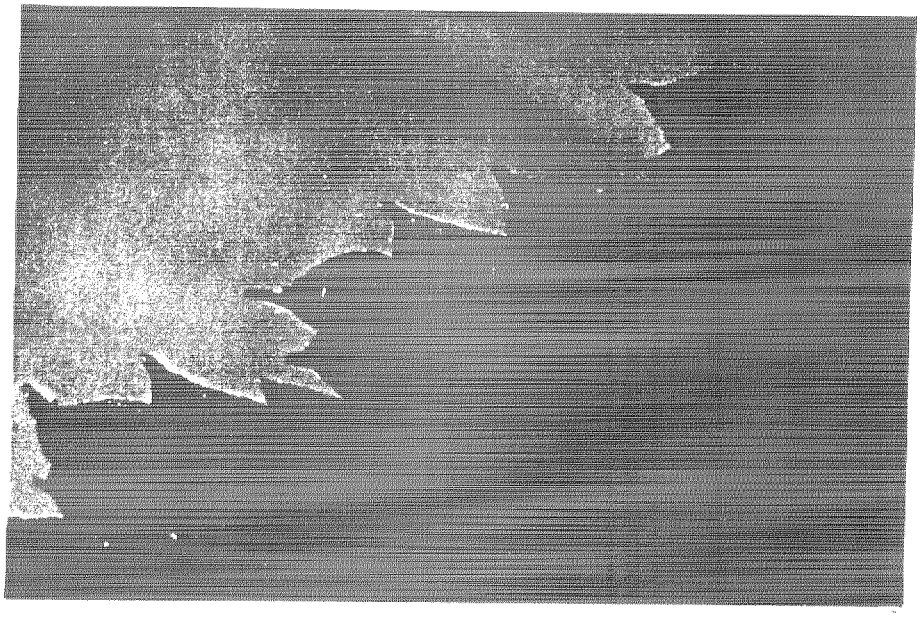
FIG. 4 shows the leaf serration of JEF-b1.

JEF-b1 produces a moderate number of root- and crown-suckers. During the growing season, canes are light green colored, usually unbranched, semi-erect and moderately vigorous. Thorns are sparse, green, thin and usually less than 2 mm in length (see FIG. 3). Leaves have a R.H.S. (Royal Horticultural Society of London) Colour Chart number of 22A, are trifoliolate, and pentafoliolate on vigorous primocanes. Leaf serration is more complex than other eastern american raspberries, and is similar to 'Glen Gerry', a parent. 'Glen Gerry' does not produce fall fruit and is thornless. Tips or serrations of JEF-b1 leaves form more acute angles than those on leaves of 'Heritage' and other fall bearing cultivars. JEF-b1 leaf color is dark green.

Fruit is borne on the top of the primocane in the fall season or from lateral buds at the base of winter canes. Fruit trusses are cymose clusters. Flowers are perfect and indistinguishable from other raspberry cultivars. Fruit are light yellow in color, having R.H.S. Color Chart number 143A, firm, large, and very symmetrical. Druplets are held together tightly, and druplets will often tear before they separate from their neighbors. Fruit is round-conic, has an even collar, and readily separates from its torus as do other raspberries. The cavity width is slightly smaller than in other cultivars. Fruit has a mild-sweet flavor with a banana-aromatic flavor developing in cooler climates.

The plant is field resistant to many common pests and diseases in the eastern United States, e.g. mildew, anthracnose, leaf rust, and verticillium wilt. The plants' reaction to *Phytophthora fragarae* root rot is probably moderately resistant. Fruit is only moderately resistant to rot.

Fruit Production

JEF-b1 has been tested in a replicated trial in Cream Ridge, N.J., and in Rock Hall, Pa. The following data were collected in the summer/fall of 1994 and 1995. Early yield refers to fruit picked before Sep. 1, 1994.

TABLE 1

Comparison of fresh fruit characteristics of 'Heritage', 'Goldie' and JEF-b1

| | | JEF-b1 | Heritage | Goldie |
|---|---|---|---|---|
| Yield in thousands of lbs/acre | NJ, 1994 | 3.9 | 4.9 | — |
| | NJ, 1995 | 2.6 | 8.1 | — |
| | PA, 1995 | 1.2 | 1.4 | 1.4 |
| Fruit Weight in grams/fruit | NJ, 1994 | 2.0 | 1.7 | — |
| | PA, 1995 | 2.2–2.7 | 1.4–1.9 | 1.5–1.7 |
| Early Yield (thousand lbs/acre) | NJ | 0.8 | 0.1 | — |
| Fruit Cavity Radius (mm) | | 6.4 | 7.7 | — |
| Fruit Width (cm) | | 1.63 | 1.55 | — |
| Fruit Length (cm) | | 1.92 | 1.40 | — |
| Seed weight (mg) | | 1.87 | 1.16 | — |

In 1994, JEF-b1 fruit did not show yellow rust.

Nucleic Acid Fingerprinting

The unique DNA fingerprint of JEF-b1 was produced by random amplified polymorphic DNA (RAPD) analysis. Leaf DNA's were isolated using a modified CTAB (hexadecyl trimethyl ammonium bromide) procedure (Rowland and Nguyen, 1993, *Biotechniques* 14: 735–736) without the final PEG precipitation step.

Amplification reactions were performed in volumes of 25 μl using a procedure described in Levi et al., 1993, HortScience, 28:1188-1190). The reagents and conditions included 50 mM Tris HCL-pH 9.0, 20 mM NaCl, 4 mM $MgCl_2$, 1% Triton X-100, 0.1% Gelatin, 0.2 μM primer (Promega 80-34), 200 μM of each dNTPs, 0.028 units/μl of Taq DNA polymerase (Promega Corporation, Madison, Wis.) and 1 mg/ml of template DNA. The oligonucleotide primer was synthesized by Promega Inc, Madison, Wis.

DNA was amplified in a MJ programmable thermal control (Model PTC-100, MJ Research, Watertown, Mass.) programmed for 51 cycles of 40 sec at 94° C., 70 sec at 48° C., and 2 min at 72° C. Amplification products were analyzed by electrophoresis at 90 constant volts in 1.4% Sigma agarose gels with 0.5×TBE buffer. DNA bands were detected under UV light after staining with ethidium bromide and visualized by producing a negative image on a computer. Comparison of bands with a 123 base pair ladder indicate the presence of JEF-b1 bands at 370, 600, 710, 840, 980, 1150, 1250, and 1730 bp; 'Ruby' bands at 550, 600, 980, 1150, and 1730 bp; and 'Heritage' bands at 600, 840, 980, and 1150 bp.in primer 80-34. The existence of bands unique to JEF-b1 under the conditions of this test is proof of fundamental genetic differences between JEF-b1 and 'Ruby' and 'Heritage'. 'Goldie' and 'Kiwigold', two yellow-fruited, fall-bearing clones of 'Heritage', produce bands identical to 'Heritage', and are therefore also genetically different from JEF-b1. The thorns on 'JEF-b1' distinguishes it from 'Glen Gerry', a parent, and its yellow, large and cohesive fruit and leaf serration distinguishes it from 'Amity', its other parent.

What is claimed is:

1. A new and distinct fall bearing red raspberry plant known as 'Anne' as described herein, illustrated and identified by the characteristics set forth above.

* * * * *

PLT-204 SR
C5203 OR PP 010,411

DNA Bands for 'Lauren', 'Titan', 'Ruby', 'Caroline', 'Heritage', and 'Anne'